(12) United States Patent
Salonen et al.

(10) Patent No.: US 7,211,387 B2
(45) Date of Patent: May 1, 2007

(54) DNA MOLECULE ENCODING A VARIANT PARAOXONASE AND USES THEREOF

(75) Inventors: Jukka T. Salonen, Jännevirta (FI);
Marja Marchesani, Kuopio (FI);
Tomi-Pekka Tuomainen, Kuopio (FI);
Jari Kaikkonen, Kuopio (FI)

(73) Assignee: OY Jurilab Ltd., Kuopio (FI)

( * ) Notice: Subject to any disclaimer, the term of this patent is extended or adjusted under 35 U.S.C. 154(b) by 418 days.

(21) Appl. No.: 10/691,562

(22) Filed: Oct. 24, 2003

(65) Prior Publication Data
US 2004/0142349 A1  Jul. 22, 2004

(51) Int. Cl.
*C12Q 1/68* (2006.01)
*C12Q 1/34* (2006.01)
*C12Q 1/44* (2006.01)
*C12N 9/16* (2006.01)
*C12N 9/18* (2006.01)
*C07H 21/04* (2006.01)

(52) U.S. Cl. .............................. 435/6; 435/18; 435/19; 435/196; 435/197; 536/23.2

(58) Field of Classification Search .................... 435/6, 435/197; 536/23.2, 24.31
See application file for complete search history.

(56) References Cited

FOREIGN PATENT DOCUMENTS

WO       WO0128365 A1       4/2001

OTHER PUBLICATIONS

Watson et al. (Mar. 2001) Pharmacogenetics, vol. 11, pp. 123-134.*
Marchesani et al. (Jun. 4, 2003) Journal of the National Cancer Institute, vol. 95, No. 11, pp. 812-818.*
Salonen et al., Supplement II Circulation, vol. 104, No. 17, pp. 3794, (Oct. 23, 2001).
La Du et al., Chem. Biol. Interactions, vol. 87, pp. 25-34, (1993).
Clendenning et al., Genomics, vol. 35, pp. 586-589, (1996).
Primo-Parmo et al., Genomics, vol. 33, pp. 498-507, (1996).
Leviev et al., Arterioscler Thromb. Vasc. Biol., vol. 20, pp. 516-521, (2000).
Brophy et al., Pharmacogenetics, vol. 11, pp. 77-84, (2001).
Wood et al., J. Steroid Biochem. Molec. Biol., vol. 59, pp. 472-473, (1996).
Zabetian et al., Am. J. Hum. Genet., vol. 68, pp. 515-522, (2001).
Masato et al., Jap. J. of Electrophoresis, vol. 38, No. 3, pp. 81-88, (1994).
Kolosha et al., Human Mutation, vol. 15, pp. 447-453, (2000).
Yamada et al., Biochemical and Biophysical Res. Comm., vol. 236, No. RC977047, pp. 772-775, (1997).
Maekawa et al., Clinical Chemistry, vol. 43, No. 6, pp. 924-929, (1997).
Landegren et al., Genome Research, vol. 8, pp. 769-776, (1998).
J. T. Salonen et al., Diabetes, vol. 47, pp. 270-275 (Feb. 1998).
S. A. Everson et al., Psychosomatic Medicine, 58: 113-121 (1996).
L. Teppo et al., Acta Oncologica, vol. 33, No. 4, pp. 365-369 (1994).
M. Ihanainen et al., Nutrition Research, vol. 9, pp. 597-604 (1989).
J. T.Salonen et al., BMJ, vol. 311, pp. 1124-1127 (Oct. 1995).
T. A. Lakka et al., New England Journal of Medicine, 330:1549-1554 (Jun. 1994).
J. T. Salonen et al., Circulation, vol. 86, No. 3, pp. 803-811 (Sep. 1992).
J. T. Salonen et al., Annals of Clinical Research, 20: 46-50 (1988).
M. I. Mackness et al., The Lancet, vol. 349, pp. 851-852 (Mar. 1997).
M. I. Mackness et al., Biochem. J., 245: 293-296 (1987).
M. I. Mackness et al., FEBS, vol. 286, No. 1, 2, pp. 152-154 (Jul. 1991).
B. N. La Du et al., Chem.-Biol. Interactions, 87 (1993) 25-34.
R. Humbert et al., Nature Genetics, vol. 3, pp. 73-76 (Jan. 1993).
H. G. Davies et al., Nature Genetics, vol. 14, pp. 334-336 (Nov. 1996).
D. M. Shih et al., Nature, vol. 394, pp. 284-287 (Jul. 1998).
M. C. Blatter Garin et al., J. Clin. Invest., vol. 99, No. 1, pp. 62-66 (Jan. 1997).
B. Mackness et al., British J. of Pharm., vol. 122:265-268 (1997).
M. I. Mackness et al., Atherosclerosis, 86: 193-199 (1991).
B. Mackness et al., The Lancet, vol. 353, No. 9151 (Feb. 1999).
M. I. Mackness et al., Current Opinion in Lipidology, 7:69-76 (1996).

* cited by examiner

*Primary Examiner*—Elizabeth Slobodyansky
(74) *Attorney, Agent, or Firm*—Birch, Stewart, Kolasch & Birch, LLP

(57)       ABSTRACT

This invention is directed to a DNA sequence comprising a nucleotide sequence encoding a variant paraoxonase protein and to said variant paraoxonase protein as well as a method and a kit for detecting a risk of cancer, coronary or cerebrovascular disease, hypertension, type 2 diabetes, dementia, joint arthrosis, cataract, or sensitivity to organophosphorus compounds in a subject, the method comprising isolating genomic DNA from said subject, determining the allelic pattern for the codon 102 of the paraoxonase encoding PON1 gene in the genomic DNA, identification of Ile101Val mutation indicating said risk being increased and for targeting paraoxonase activity modulating therapies. Further this invention relates to transgenic animals comprising a human DNA molecule encoding said variant paraoxonase and to a method of phenotype-targeted gene sequencing.

6 Claims, No Drawings

DNA MOLECULE ENCODING A VARIANT PARAOXONASE AND USES THEREOF

This application claims priority under 35 U.S.C. § 120 of application Ser. No. 09/811,673 filed on Mar. 20, 2001 and issued as U.S. Pat. No. 6,740,746B2 on May 25, 2004, the contents of which are hereby incorporated by reference.

FIELD OF THE INVENTION

The present invention relates to a DNA molecule encoding a variant human paraoxonase (EC 3.1.1.2), and to said variant paraoxonase protein. The present invention also relates to a method for detecting or predicting the risk of, or predisposition to, cancer, coronary and cerebrovascular diseases, type 2 diabetes, hypertension, dementia, arthrosis, cataract and sensitivity to organophosphorus compounds in a subject, as well as to a kit or assay for carrying out the said method. This invention also relates to targeting paraoxonase enhancing treatments and to transgenic animals comprising a human DNA molecule encoding said variant paraoxonase and to a method of mutation search.

BACKGROUND OF THE INVENTION

The publications and other material used herein to illuminate the background of the invention are incorporated by reference.

Oxidative stress and free radicals have been implicated in the etiology of a number of diseases, including cancers, coronary heart disease, cerebrovascular disease, type 2 diabetes, hypertension, dementia and cataract. The human body has a number of endogenous free radicals scavenging systems which have genetic variability. The human serum paraoxonase (PON) is an enzyme carried in the high-density lipoprotein that contributes to the detoxification of organophosphorus compounds but also of toxic products of lipid peroxidation.[1-9] The paraoxonase hydrolyzes the toxic metabolites of several organophosphorus (OP) insecticides, pesticides and nerve agents.

The PON1 gene is polymorphic in human populations and different individuals also express widely different levels and activities of the paraoxonase enzyme, which is the protein product coded by the gene.[3,5-7]

Several polymorphisms are currently known in human PON1. The Gln191 Arg poly-morphism was the first mutation of PON1 reported.[3,6] The second one is the Met54Leu.[3] Both these polymorphisms have been shown to affect serum PON activity.[6,10,11]

Transgenic animals and with lowered paraoxonase activity can be used e.g. to test the effects of organophosphorus compounds, such as insecticides, pesticides and war agents, drugs that affect paraoxonase activity, other antioxidative compounds and drugs, and liver enzyme activity inducing agents.

A lot of methodological work has been done to locate disease-causing genes or candidate genes. However, there are no previous methodological studies concerning the methods of how to promote the search for mutations in a given or known candidate gene. To facilitate the finding of mutant DNA sequences, we developed a new method of phenotype-targeted gene sequencing.

SUMMARY OF THE INVENTION

One object of this invention is to provide a DNA sequence of a variant human PON1 gene and the amino acid sequence of the corresponding variant paraoxonase protein. Another object of the invention is to provide a method for screening a subject to assess if such subject is at risk of cancer, coronary or cerebrovascular disease, hypertension, type 2 diabetes, dementia, joint arthrosis or eye cataract, or at risk of being sensitive to organophosphate toxicity. The invention is also directed to a kit or an assay for said method, as well as to a probe for use in said method or kit. A further object of the invention is to provide a method for targeting a paraoxonase enhancing treatment for example for the above mentioned diseases and for organophospate poisoning, and/or for assessing the effectiveness of paraoxonase modifying treatments. A fourth object of the invention is to provide a transgenic animal with a gene encoding a variant paraoxonase. A fifth object of the invention is to provide a method for rapid search of gene mutations. These and further objects will be evident from the following description and claims.

According to one aspect, the invention concerns a DNA sequence comprising a nucleotide sequence encoding a variant paraoxonase protein with the Ile102Val mutation. The said mutation can, in the alternative, be named also Ile101Val, if the start codon atg (Met) is not included in the count. In the following description and claims, reference is made to the Ile102Val mutation, but said reference means within the scope of the invention in the alternative the Ile101Val mutation in case the alternative way of counting is used. The invention also concerns a variant paraoxonase protein with the Ile102Val mutation.

According to further aspect, the invention concerns a method for screening a subject to determine if said subject is a carrier of a variant gene encoding a variant paraoxonase, by determining the allelic pattern for the codon 102of the human PON1 gene, i.e. to determine if the said subject is a carrier of the Ile102Val mutation.

Specifically such a method comprises the steps of
a) providing a biological sample of the subject to be screened, and
b) providing an assay for detecting in the biological sample the presence of the Ile102Val or Val102Val genotype of the human PON1 gene.

The assay result can be used for assessing the subject's risk to develop a low paraoxonase expression related disease such as cancer, coronary or cerebrovascular disease, type 2 diabetes, hypertension, dementia, arthrosis or cataract or sensitivity to organophosphorus compounds, and/or for assessing the effectiveness of paraoxonase-inducing therapy in a subject, whereby identification of a Ile102Val mutation being indicative of said risk being increased or effectiveness being modulated.

The present invention is thus directed to a method for detecting a risk of cancer, coronary or cerebrovascular disease, type 2 diabetes, hypertension, dementia, arthrosis or cataract in a subject, comprising isolating genomic DNA from said subject, determining the allelic pattern in the exon number 4 in the codon number 102 of the paraoxonase encoding PON1 gene in the genomic DNA, and identification of Ile102Val mutation indicating said risk being increased.

The present invention is also directed to a method for assessing the effectiveness of paraoxonase inducing therapy of a subject, comprising isolating genomic DNA from said subject, determining the allelic pattern in the exon number 4 in the codon number 102 of the paraoxonase encoding PON1 gene in the genomic DNA, and identification of Ile102Val mutation indicating said effectiveness being modulated, e.g. reduced.

The invention is also directed to a method for determining the presence or absence in a biological sample of a DNA sequence comprising a nucleotide sequence encoding a variant paraoxonase protein, the method comprising isolating genomic DNA from said subject, determining the allelic pattern in the exon number 4 in the codon number 102 of the paraoxonase encoding PON1 gene in the genomic DNA, and identification of Ile102Val mutation indicating the presence of said DNA sequence.

The techniques for carrying out such a method and presented here are intended to be non-limiting examples. One skilled in the art will readily appreciate that other methods for detection of the variant DNA sequence can be used, developed or modified.

One detection method is minisequencing which is based on a minisequencing reaction, in which an oligonucleotide that ends one nucleotide upstream the variant nucleotide, is enzymatically elongated by one nucleotide that is complementary to either the variant or the wild type nucleotide in the target sequence, and this added labelled nucleotide is detected. Such label can be, for example, radioactive or fluorescent label.

Another detection method is based on appearance or disappearance of an enzymatic cleavage site by the variant nucleotide. This kind of detection can be performed by first amplificating the target nucleotide sequence by a polymerase chain reaction with primers that flank the variant nucleotide, and then digesting the reaction product with a restriction endonuclease that recognises only the variant or only the wild-type sequence, producing DNA fragments of different length for each. These fragments may be recognised, for example, by gel electroforesis with DNA staining.

Yet another detection method is the oligonucleotide ligation assay, in which two allele specific oligonucleotide probes and one common oligonucleotide probe are used to distinguish between the variant and wild-type nucleotide. In this method, the target sequence is hybridised with the three oligonucleotide probes, and the probe pair that is complementary to the target sequence is joined enzymatically at the site of the variant nucleotide. The detection of the two alleles is based on differing labels, for example fluorescent labels of different colour, of the two allele specific oligonucleotide probes.

Furthermore, a detection method is the single stranded conformational analysis, in which the different alleles of a target sequence are identified on the basis of a difference in the electrophoretic mobility of the two alleles. In this method, the variant and wild-type target sequences that are in single stranded form, migrate with different speed through an electrophoresis matrix. Preferably, the target sequence is first amplified with a polymerase chain reaction, and the product is labelled for detection by radioactive or fluorescent label.

Yet furthermore, a detection method is sequencing, in which each nucleotide of the target sequence is identified. The variant allele is identified by the variant nucleotide.

Another detection method is allele specific hybridisation, in which an oligonucleotide probe is hybridised with the target sequence, and in which the probe is complementary only to the variant or wild-type allele. Preferably, two allele specific probes are used simultaneously to identify both alleles. Detection of a successful hybridisation and the determination of a genotype is based on detection of the probe-target duplex, on a basis of enzymatic colour reaction, or based on a label on the probe or on the target, for example a radioactive or a fluorescent label.

The present invention is also directed to a kit or assay for detecting a risk of cancer, coronary or cerebrovascular disease, type 2 diabetes, hypertension or dementia and sensitivity to organophosphorus compounds, and/or for assessing the need for or effectiveness of paraoxonase inducing therapy in a subject, comprising means for determining the allelic pattern in the exon number 4 in the codon 102 of the paraoxonase encoding PON1 gene in a genomic DNA sample. The assay may be a part of a DNA macroarray or microarray or a DNA chip or a DNA slide, which is intended for the detection of multiple gene mutations.

According to a further aspect, the present invention concerns a transgenic animal which carries a human DNA sequence comprising a nucleotide sequence encoding a variant human paraoxonase protein.

According to a farther aspect, the present invention concerns the method of phenotype-targeted gene sequencing.

DETAILED DESCRIPTION OF THE INVENTION

In order to find new previously unknown functional mutations in the human PON1 gene, phenotype-targeted hierarchial sequencing was used. The serum paraoxonase activity was determined for over 1000 serum samples. DNA samples of 10 persons with the lowest PON activity were first chosen for sequencing and they were sequenced through in all 9 exons with an ABI PRISM 3100 Genetic Analyzer (Applied Biosystems). A new previously unknown human PON1 mutation was found in codon number 102 in exon number 4, called PON Ile102Val, causing the change ATC to GTC; Ile to Val. After the new mutation was found, DNA samples of 100 men with low paraoxonase activities were sequenced, and the mutation was present in 9.0% of the subjects. Finally 1,595 DNA samples available in the KIHD (Kuopio Ischaemic Heart Disease Risk Factor Study) cohort were genotyped and the new mutation was found for 61 persons; 3.8% of the random population sample of men.

A polymerase chain reaction was carried out as follows: the genomic DNA was amplified in eight parts specific for the PON1-gene and for its exons 1 to 9. Eight different amplifications were made, with eight different PCR primer pairs (SEQ ID NO:5–20); one pair for each exon except for the exons 2 and 3 which were amplified together. All 9 exons were sequenced.

The kit or assay for use in the method according to the invention preferably contains the various components needed for carrying out the method packaged in separate containers and/or vials and including instructions for carrying out the method. Thus, for example, some or all of the various reagents and other ingredients needed for carrying out the determination, such as buffers, primers, enzymes, control samples or standards etc can be packaged separately but provided for use in the same box. Instructions for carrying out the method can be included inside the box, as a separate insert, or as a label on the box and/or on the separate vials.

Experimental Section

Polymerase Chain Reaction

The method according to the invention for determining the allelic pattern of the codon in question is preferably carried out as a polymerase chain reaction, in accordance with known techniques.[3] The PCR primer pair for human paraoxonase (PON 1) exon number 4 was as follow: 5'-CTCCTCCATGGTTATAAGGG-3' (SEQ ID NO:9) and 5'-CCCAGAGTAAGAACATTATTC-3' (SEQ ID NO: 10)

(product size 315 bp). The primers were designed by Marja Marchesani and they were delivered by the AIV Institute, sequencing services (Kuopio, Finland). PCR amplification was conducted in a 25 µl volume containing 150 ng genomic DNA (extracted from peripheral blood), 10×PCR buffer, dNTP (10 mM of each), 20 pmol/µl of each primer, DNA-polymerase (2U/µl) (DyNAzyme™ DNA polymerase kit, Finnzymes, Espoo, Finland). Samples were amplified with a Biometra UNO programmable thermoblock (Biometra, Göttingen, Germany) with PCR programme conditions as follows: 95° C. for 3 minutes, Repeat following for 30 cycles: 95° C. for 30 seconds, 58° C. for 45 seconds, 72° C. for 45 seconds, 72° C. for 5 minutes, 4° C. hold. Amplified PCR-products were purified using the QIAquik PCR purification kit (QIAGEN, Valencia, Calif.).

Sequencing

Sequencing was made using a ABI PRISM® 3100 Genetic Analyzer (Applied Biosystems, Foster City, Calif.). The ABI PRISM® 3100 Genetic Analyzer is a fluorescence-based DNA analysis system of capillary electrophoresis with 16 capillaries operating in parallel, fully automated from sample loading to data analysis.

The sequencing reactions were made by using the DNA Sequencing Kit; Big Dye™ Terminator cycle sequencing v.2.0 ready reactions with ampliTaq® DNA polymerase (Fs ABI PRISM®, PE Biosystems, Foster City, Calif.). The sequencing primers were the same as the PCR primers: 5'-CTCCTCCATGGTTATAAGGG-3' (SEQ ID NO:9) or 5'-CCCAGAGTAAGAACATTATTC-3' (SEQ ID NO: 10). Cycle sequencing was made in the GeneAmp PCR System 9600 (PE Biosystems) with the programme as follows: Repeat the following for 25 cycles; rapid thermal ramp to 96° C., 96° C. for 10 seconds, rapid thermal ramp to 50° C., 50° C. for 5 seconds, rapid thermal ramp to 60° C., 60° C. for 4 minutes (to perform cycle sequencing under standard conditions, ABI PRISM® 3100 Genetic Analyzer Sequencing Chemistry Guide, Applied Biosystems).

Dye Terminator Removal and sequencing reaction clean-up was made using multiscreen 96-well filtration plates (Multiscreen® -HV clear plates, Millipore, Bedford, Mass.). After purification the samples were denaturated at 94° C. for 1 min and the sequencing was done using the ABI PRISM® 3100 Genetic Analyzer using MicroAmp optical 96-well reaction plates (Applied Biosystems).

Genotyping

Specifically genotyping was done by extracting DNA from EDTA blood with a salting-out method after lysing red cells with 10 mM NaCl/10 mM EDTA. The 315 bp exon 4 PCR-product of the PON1 gene was digested with Sau 3 AI restriction endonuclease (New England BioLabs, Beverly, Mass.), mixed with 6× loading dye solution and run in 2.0 % agarose gel electroforesis. Identification of normal and mutant forms was based on different electrophoretic migration rates of the restriction fragments, resulting in distinct bands (normal form (Ile102Ile); 196 bp, 100 bp, 19 bp, heterozygote form (Ile102Val); 215 bp, 196 bp, 100 bp, 19 bp and homozygote form (Val102Val); 215 bp, 100 bp).

Determination of Serum PON Activity

Serum paraoxonase activity was measured based on its capacity to hydrolyse paraoxon. 100 µl of diluted serum (25-fold dilution in TRIS-HCl buffer, pH 8.0) was mixed with 100 µl of paraoxon (Paraoxon, Dr. Ehrensdorfer GmbH, Augsburg, Germany) (0.1 g in 66.1 ml of TRIS-HCl buffer, pH 8.0). Formation of p-nitrophenol was monitored photometrically at 405 nm (at 30 C), as previously described.[12]

Testing for the Risk of Cancer, Coronary or Cerebrovascular Disease, Type 2 Diabetes or Hypertension The study subjects were from the "Kuopio Ischaemic Heart Disease Risk Factor Study" (KIHD), a prospective population study to investigate risk factors for cardiovascular diseases, type 2 diabetes, hypertension, dementia and cancers.[13-17,19,20] The KIHD study protocol was approved by the Research Ethics Committee of the University of Kuopio, Finland. The study sample comprised men from Eastern Finland aged 42, 48, 54 or 60 years. A total of 2,682 men were examined during 1984–89. All participants gave a written informed consent. A DNA sample was available for 1595 men.

All cancer cases in the health care have been reported to a national cancer registry in Finland since 1953.[18] Our study cohort was record-linked to this cancer registry data by using the unique personal identification code (social security number) that all Finns have. Deaths in the cohort were obtained by record linkage to the national death certificate registry and hospitalizations by record linkage to the national hospital discharge registry. The history of hypertension and diabetes was assessed at baseline and at a 4-year follow-up by self-administered questionnaire, checked by an interviewer. Both at baseline and at the 4-year follow-up examination, blood pressure and fasting blood glucose were measured using identical methods both at baseline and at the 4-year follow-up.[16,20]

The first occurrence of cancer after the KIHD baseline examination was registered in the cancer registry during 1984–97 for 60 cohort members. The primary site was prostate for 15 cancers. There were 1246 men with no prior CHD or cerebrovascular disease. Of these, 342 were smokers and 904 non-smokers. Of the smokers, 21 died of a cardiovascular cause by the end of 1998. Of the 515 men examined at baseline during 1984–86, 36 developed an arthrosis (ICD-10 M15–M19) by the end of 1998. Of the 1107 non-smoking men, 23 developed a cataract (ICD-10 H26–H29) by the end of 1998.

The association of the PON1 Ile102Val genotype with the risk of hypertension and diabetes was studied among 1038 men who were re-examined 4 years after the baseline examination, see references 15,19 for details of the re-examination. For the analysis of the incidence of hypertension, hypertensive (history of hypertension, antihypertensive medication or systolic BP 160 mmHg or more or diastolic BP 95 mmHg or more) and obese (body mass index 29 kg/m$^2$ or more) men and those with a history of cancer were excluded, leaving 488 men for the analysis. For the analysis of the incidence of type 2 diabetes, men with a history of cancer or prevalent diabetes at baseline (fasting blood glucose 6.7 mmol/l or more or treatment for diabetes) were excluded, after which exclusion there were 967 men for the analysis.

Lipoproteins were separated from fresh serum samples using ultracentrifugation and precipitation.[13,14] Cholesterol and triglyceride concentrations were measured enzymatically, plasma ascorbate and lipid-standardized plasma vitamin E concentration by HPLC methods[16,20] serum ferritin and apolipoproteins with a RIA[12]. The maximal oxygen uptake, a measure of cardiorespiratory capacity, was measured directly during a symptom limited exercise test.[15] Information regarding medical history and medications was obtained by interview. Smoking was recorded using a self-administered questionnaire and the dietary intake of nutrients was estimated by four-day food recording.[17]

Risk-factor adjusted relative risks of cancer, prostate cancer and cardiovascular death were estimated by multivariate Cox proportional hazards modelling and those of incident hypertension and incident diabetes by multivariate logistic regression modelling. Covariates were selected by forward step-up modelling, using P-value of 0.10 as entry criterium. Missing values in covariates were replaced by grand means. Tests of statistical significance were one-sided. The statistical analyses were performed with SPSS version 10.0 for Windows.

Of all members of the study cohort, 61 (3.8%) were Val allele carriers of the PON1 gene Ile102Val polymorphism. To ascertain the penetrance of the PON1 102 mutation, serum PON activity was measured at the 11-year re-examination for 783 cohort members as described above. The mean activity was 168.7 U/l in the wild Ile-Ile homozygotes vs. 70.7 U/l in 102Val carriers (p<0.001). In a 2-way analysis of variance (n=782), the Ile102Val polymorphism (p<0.001) was a stronger predictor of paraoxonase activity than the Leu54Met polymorphism (p=0.016).

In a multivariate Cox model adjusting for the strongest other risk factors in this cohort: maximal oxygen uptake, dietary vitamin C intake, smoking status (current smoker vs. non-smoker), body mass index, serum lipoprotein (a), dietary iron intake and apolipoprotein B, the relative risk of any cancer in the 102Val carriers was 2.4 (90% CI 1.0 to 5.5, p=0.052), compared with 102Ile homozygotes (p<0.001 for the model, Table 1). This association was stronger in 462 smokers with 24 incident cancers (RR 3.2, 90% CI 0.9–10.8, p=0.060) than in 1107 nonsmokers with 36 incident cancers (RR1.5, 90% CI 0.4–4.8, p=0.300).

The risk of prostate cancer was 4.9-fold (90% CI 1.4–17.4, p=0.021) among 102Val carriers compared with the wild homozygotes (Table 1). The model included maximal oxygen uptake, place of residence, serum $HDL_2$ cholesterol, histories of stroke and any atherosclerosis-related disease, cholesterol lowering medication, dietary iron intake and diastolic blood pressure as covariates.

The risk of cataract was examined in non-smokers, because smoking is an overwhelmingly powerful risk factor for cataracts. Among the 1107 non-smokers, the 102Val carriers had a 3.8-fold (90% CI 1.1–13.0, p=0.038) risk of cataract in a Cox model adjusting for blood glucose, blood leukocyte count, hair mercury content and the examination year 1989 (Table 1).

Smoking men who were PON1 102Val carriers had a 4.9-fold (90% CI 1.3–18.1, p=0.023) risk of cardiovascular death, compared with the 102Ile homozygotes (Table 1). The covariates included in the model were maximal oxygen uptake, history of any atherosclerosis-related disease, place of residence, serum apolipoprotein B level, plasma lipid-standardized vitamin E concentration (protective), examination year 1988 (vs. any other), and the serum fatty acid ratio (saturated/sum of monoenes and polyenes).

Among non-obese men, the PON1 102Val carriers had a 2.9-fold (90% CI 1.3–6.5, p=0.019) risk of hypertension, compared with non-carriers (Table 2), when adjusting for serum triglycerides, CHD in exercise test, dietary vitamin E intake (protective), frequency of hangovers, dietary retinol intake, and PON1 54 polymorphism.

As arthrosis is a chronic, gradually developing disease, only men examined in the first three years (1984–6) were included in a logistic regression analysis (Table 2). The carriers of the 102Val mutation had a 4.0-fold (90% CI 1.3–12.4, p=0.022) risk of developing an arthrosis during the follow-up, when adjusting for waist-to-hip circumference ratio, serum ferritin and dietary intakes of vitamin E and vitamin C.

Men with an 102Val allele had a 3.2-fold (90% CI 1.1–9.3, p=0.039) risk of type 2 diabetes, as compared with 102Ile homozygotes. Covariates in the model were serum fatty acid ratio (defined above), serum ferritin concentration and family history of obesity.

The Mini Mental State Examination was used to assess the presence of cognitive impairment and the degree of dementia of the KIHD participants aged 65–71 during 1998–2000. The test examines orientation (ten items), registration (three items), attention and calculation (five items), recall (three items) and language (nine items). A correct response to each item scores 1 (incorrect 0), which are summed to give a potential maximum score of 30. Higher scores indicate better cognitive function. The mean score was 25.5 (SD 2.5) among the 26 carriers of the PON102 Val allele and 26.4 (SD 2.2) among 338 non-carriers for whom data were available (one-sided p=0.031 in t-test, exact p=0.045). The Mini Mental State examination score was directly associated Pearson's correlation coefficient 0.14, p=0.008, n=359) with serum paraoxonase enzyme activity. This association remained statistically significant (p=0.012) after a statistical adjustment for age and socio-economic status, which were other strongest predictors of the score.

TABLE 1

The association of PON1 102Val carrier status with the risk of any cancer, prostate cancer and cardiovascular death in multivariate Cox regression models in healthy men

| Disease | Number of men free of disease at entry | | Relative risk (90% CI)* | p-value |
|---|---|---|---|---|
| | At the start of follow-up | Who developed disease | | |
| Any cancer** | 1569 | 60 | 2.35 (1.00, 5.54) | 0.052 |
| Prostate cancer** | 1569 | 15 | 4.86 (1.36, 17.36) | 0.021 |
| Cataract** | 1107 non-smokers | 23 | 3.79 (1.10, 12.98) | 0.038 |
| Cardiovascular death*** | 342 smokers | 21 | 4.93 (1.34, 18.10) | 0.023 |

*The step-up models included other strongest risk factors.
**Men with a history of cancer were excluded.
***Men with a history of coronary heart disease or cerebrovascular stroke were excluded.

TABLE 2

The association of PON1 102Val carrier status with the risk of hypertension and type 2 diabetes in multivariate logistic regression models in healthy men

| Disease | Number of men free of disease at entry | | Relative risk (90% CI)* | p-value |
|---|---|---|---|---|
| | At the start of follow-up | Who developed disease | | |
| Hypertension** | 488 non-obese men | 109 | 2.85 (1.25, 6.51) | 0.019 |
| Arthrosis*** | 515 men examined in 1984–6 | 36 | 3.99 (1.29, 12.36) | 0.022 |
| Type 2 diabetes**** | 967 non-diabetic men | 33 | 3.17 (1.08, 9.28) | 0.039 |

*The step-up models included other strongest risk factors.
**Men with a history of cancer or prevalent hypertension were excluded.
***Men with a history of cancer were excluded.
****Men with a history of cancer or prevalent diabetes were excluded.

REFERENCES

1 Mackness M I, Thompson H M, Hardy A R, Walker C H. Distinction between 'A'-esterases and arylesterases. Implications for esterase classification. *Biochem J* 1987; 245: 293–6
2 Mackness M I, Arrol S, Durrington P N. Paraoxonase prevents accumulation of lipoperoxides in low-density lipoprotein. *FEBS Lett* 1991; 286: 152–4.
3 La Du B N, Adkins S, Kuo C L, Lipsig D. Studies on human serum paraoxonase/arylesterase. *Chem Biol Interact* 1993 June; 87 (1–3):25–34
4 Humbert R, Adler D A, Disteche C M, Hassett C, Omiecinski C J, Furlong C E. The molecular basis of the human serum paraoxonase activity polymorphism. *Nature Genet* 1993; 3: 73–6.
5 Davies H G, Richter R J, Keifer M, Broomfield C A, Sowalla J, Furlong C E. The effect of the human serum paraoxonase polymorphism is reversed with diazoxon, soman and sarin. *Nature Genet* 1996; 14: 334.
6 Mackness M I, Mackness B, Durrington P N, Connelly P W, Hegele R A. Paraoxonase: biochemistry, genetics and relationship to plasma lipoproteins. *Curr Opin Lipidol* 1996; 7: 69–76.
7 Mackness M I, Arrol S, Mackness B, Durrington P N. Alloenzynes of paraoxonase and effectiveness of high-density lipoproteins in protecting low-density lipoprotein against lipid peroxidation. *Lancet* 1997; 349: 851–2.
8 Mackness B, Durrington P N, Mackness M I. Polymorphisms of paraoxonase genes and low-density lipoprotein peroxidation. *Lancet* 1999; 353: 468–9.
9 Shih D M, Gu L, Xia Y-R, et al. Mice lacking serum paraoxonase are susceptible to organophosphate toxicity and atherosclerosis. *Nature* 1998; 394: 284–7.
10 Garin M C, James R W, Dussoix P, et al. Paraoxonase polymorphism Met-Leu54 is associated with modified serum concentrations of the enzyme. A possible link between the paraoxonase gene and increased risk of cardiovascular disease in diabetes. *J Clin Invest* 1997; 99: 62–6.
11 Mackness B, Mackness M I, Arrol S, Turkie W, Durrington P N. Effect of the molecular polymorphisms of human paraoxonase (PON1) on the rate of hydrolysis of paraoxon. *Br J Pharmacol* 1997; 122: 265–8.
12 Mackness M I, Harty D, Bhatnagar D, Winocour P H, Arrol S, Ishola M, Durrington P N. Serum paraoxonase activity in hypercholesterolemia and insulin-dependent diabetes mellitus. *Atherosclerosis* 1991; 86: 193–9.
13 Salonen J T. Is there a continuing need for longitudinal epidemiologic research?—The Kuopio Ischaemic Heart Disease Risk Factor Study. *Ann Clin Res* 1988; 20: 46–50.
14 Salonen J T, Nyyssönen K, Korpela H, Tuomilehto J, Seppänen R, Salonen R. High stored iron levels are associated with excess risk of myocardial infarction in Eastern Finnish men. *Circulation* 1992; 86: 803–11.
15 Lakka T A, Venäläinen J M, Rauramaa R, Salonen R, Tuomilehto J, Salonen J T. Relation of leisure-time physical activity and cardiorespiratory fitness to the risk of acute myocardial infarction. *N Engl J Med* 1994; 330: 1549–54.
16 Salonen J T, Nyyssönen K, Tuomainen T-P, Mäenpää P H, Korpela H. Kaplan G A, Lynch J, Helmrich S P, Salonen R. Increased risk of non-insulin dependent diabetes mellitus at low plasma vitamin E concentrations: a four year follow-up study in men. *Brit Med J* 1995; 311: 1124–7.
17 Ihanainen M, Salonen R, Seppänen R, Salonen J T. Nutrition data collection in the Kuopio Ischaemic Heart Disease Risk Factor Study: Nutrient intake of middle-aged eastern Finnish men. *Nutr Res* 1989; 9: 89–95.
18 Teppo L, Pukkala E, Lehtonen M. Data quality and quality control of a population-based cancer registry. Experience in Finland. *Acta Oncologica* 1994; 33: 365–9.
19 Everson S A, Goldberg D E, Kaplan G A, et al. Hopelessness and risk of mortality and incidence of myocardial infarction and cancer. *Psychosom Med* 1996; 58: 113–21.
20 Salonen J T, Lakka T A, Lakka H-M, Valkonen V-P, Everson S A, Kaplan G A. Hyperinsulinemia is associated with the Incidence of hypertension and dyslipidemia in middle-aged men. *Diabetes* 1998; 47: 270–275.

The invention claimed is:

1. A method for determining the presence in a biological sample of a DNA sequence comprising a nucleotide sequence encoding a variant human paraoxonase protein, the method comprising determining the allelic sequence of the codon number 102 of a human paraoxonase (PON1) encoding gene in the genomic DNA of the sample, identification of an Ile102Val mutation indicating the presence of said DNA sequence.

2. A method for screening a subject to determine if said subject is a carrier of at least one Ile102Val mutant paraoxonase gene comprising a) providing a biological sample of the subject to be screened, b) performing an assay for detecting in the biological sample the presence of the Ile102Val mutation of the human paraoxonase (PON1) gene, c) identifying as a carrier a subject providing a sample having at least one Ile102Val mutation of the human paraoxonase gene in the genotype.

3. A method for assessing an individual's risk to develop cancer, coronary or cerebrovascular disease, hypertension, type 2 diabetes, dementia, arthrosis, or cataract or sensitivity to organophosphorus compounds, comprising a) providing a biological sample of the subject to be screened,
b) performing an assay for detecting in the biological sample the presence of the Ile102Val allele of the human paraoxonase (PON1) gene,
c) identifying as an individual having increased risk of said disease or sensitivity to an organophosphorus compound, a subject providing a sample having at least one Ile102Val allele of the human paraoxonase gene in the genotype.

4. The method according to claim 3 wherein a DNA in the biological sample is analyzed by hybridizing said DNA, or an amplification product thereof, to an immobilized nucleic acid in a multiplex format.

5. A method for assessing effectiveness of a paraoxonase agonist therapy, or of a paraoxonase inducing or enhancing therapy, in an individual comprising a) providing a biological sample of the subject to be screened,
b) performing an assay for detecting in the biological sample the presence of the Ile102Val allele of the human paraoxonase (PON1) gene,
c) identifying as an individual having reduced effectiveness of a paraoxonase agonist or paraoxonase inducing or enhancing therapy, a subject providing a sample having at least one Ile102Val allele of the human paraoxonase gene in the genotype.

6. The method according to claim 5 wherein a DNA in the biological sample is analyzed by hybridizing said DNA, or an amplification product thereof, to an immobilized nucleic acid in a multiplex format.

* * * * *

SEQUENCE LISTING

<160> NUMBER OF SEQ ID NOS: 20

<210> SEQ ID NO 1
<211> LENGTH: 1068
<212> TYPE: DNA
<213> ORGANISM: Homo sapiens
<220> FEATURE:
<221> NAME/KEY: CDS
<222> LOCATION: (1)..(1068)
<223> OTHER INFORMATION: Coding sequence for variant human paraoxonase
                        (PON1) protein

<400> SEQUENCE: 1

```
atg gcg aag ctg att gcg ctc acc ctc ttg ggg atg gga ctg gca ctc      48
Met Ala Lys Leu Ile Ala Leu Thr Leu Leu Gly Met Gly Leu Ala Leu
1               5                   10                  15 ttc agg aac cac cag tct tct tac caa aca cga ctt aat gct ctc cga      96
Phe Arg Asn His Gln Ser Ser Tyr Gln Thr Arg Leu Asn Ala Leu Arg
            20                  25                  30
```

| | | |
|---|---|---|
| gag gta caa ccc gta gaa ctt cct aac tgt aat tta gtt aaa gga atc<br>Glu Val Gln Pro Val Glu Leu Pro Asn Cys Asn Leu Val Lys Gly Ile<br>35 40 45 | | 144 |
| gaa act ggc tct gaa gac atg gag ata ctg cct aat gga ctg gct ttc<br>Glu Thr Gly Ser Glu Asp Met Glu Ile Leu Pro Asn Gly Leu Ala Phe<br>50 55 60 | | 192 |
| att agc tct gga tta aag tat cct gga ata aag agc ttc aac ccc aac<br>Ile Ser Ser Gly Leu Lys Tyr Pro Gly Ile Lys Ser Phe Asn Pro Asn<br>65 70 75 80 | | 240 |
| agt cct gga aaa ata ctt ctg atg gac ctg aat gaa gaa gat cca aca<br>Ser Pro Gly Lys Ile Leu Leu Met Asp Leu Asn Glu Glu Asp Pro Thr<br>85 90 95 | | 288 |
| gtg ttg gaa ttg ggg gtc act gga agt aaa ttt gat gta tct tca ttt<br>Val Leu Glu Leu Gly Val Thr Gly Ser Lys Phe Asp Val Ser Ser Phe<br>100 105 110 | | 336 |
| aac cct cat ggg att agc aca ttc aca gat gaa gat aat gcc atg tac<br>Asn Pro His Gly Ile Ser Thr Phe Thr Asp Glu Asp Asn Ala Met Tyr<br>115 120 125 | | 384 |
| ctc ctg gtg gtg aac cat cca gat gcc aag tcc aca gtg gag ttg ttt<br>Leu Leu Val Val Asn His Pro Asp Ala Lys Ser Thr Val Glu Leu Phe<br>130 135 140 | | 432 |
| aaa ttt caa gaa gaa gaa aaa tcg ctt ttg cat cta aaa acc atc aga<br>Lys Phe Gln Glu Glu Glu Lys Ser Leu Leu His Leu Lys Thr Ile Arg<br>145 150 155 160 | | 480 |
| cat aaa ctt ctg cct aat ttg aat gat att gtt gct gtg gga cct gag<br>His Lys Leu Leu Pro Asn Leu Asn Asp Ile Val Ala Val Gly Pro Glu<br>165 170 175 | | 528 |
| cac ttt tat ggc aca aat gat cac tat ttt ctt gac ccc tac tta caa<br>His Phe Tyr Gly Thr Asn Asp His Tyr Phe Leu Asp Pro Tyr Leu Gln<br>180 185 190 | | 576 |
| tcc tgg gag atg tat ttg ggt tta gcg tgg tcg tat gtt gtc tac tat<br>Ser Trp Glu Met Tyr Leu Gly Leu Ala Trp Ser Tyr Val Val Tyr Tyr<br>195 200 205 | | 624 |
| agt cca agt gaa gtt cga gtg gtg gca gaa gga ttt gat ttt gct aat<br>Ser Pro Ser Glu Val Arg Val Val Ala Glu Gly Phe Asp Phe Ala Asn<br>210 215 220 | | 672 |
| gga atc aac att tca ccc gat ggc aag tat gtc tat ata gct gag ttg<br>Gly Ile Asn Ile Ser Pro Asp Gly Lys Tyr Val Tyr Ile Ala Glu Leu<br>225 230 235 240 | | 720 |
| ctg gct cat aag att cat gtg tat gaa aag cat gct aat tgg act tta<br>Leu Ala His Lys Ile His Val Tyr Glu Lys His Ala Asn Trp Thr Leu<br>245 250 255 | | 768 |
| act cca ttg aag tcc ctt gac ttt aat acc ctc gtg gat aac ata tct<br>Thr Pro Leu Lys Ser Leu Asp Phe Asn Thr Leu Val Asp Asn Ile Ser<br>260 265 270 | | 816 |
| gtg gat cct gag aca gga gac ctt tgg gtt gga tgc cat ccc aat ggc<br>Val Asp Pro Glu Thr Gly Asp Leu Trp Val Gly Cys His Pro Asn Gly<br>275 280 285 | | 864 |
| atg aaa atc ttc ttc tat gac tca gag aat cct cct gca tca gag gtg<br>Met Lys Ile Phe Phe Tyr Asp Ser Glu Asn Pro Pro Ala Ser Glu Val<br>290 295 300 | | 912 |
| ctt cga atc cag aac att cta aca gaa gaa cct aaa gtg aca cag gtt<br>Leu Arg Ile Gln Asn Ile Leu Thr Glu Glu Pro Lys Val Thr Gln Val<br>305 310 315 320 | | 960 |
| tat gca gaa aat ggc aca gtg ttg caa ggc agt aca gtt gcc tct gtg<br>Tyr Ala Glu Asn Gly Thr Val Leu Gln Gly Ser Thr Val Ala Ser Val<br>325 330 335 | | 1008 |
| tac aaa ggg aaa ctg ctg att ggc aca gtg ttt cac aaa gct ctt tac<br>Tyr Lys Gly Lys Leu Leu Ile Gly Thr Val Phe His Lys Ala Leu Tyr | | 1056 |

```
                340             345             350
tgt gag ctc taa                                            1068
Cys Glu Leu
        355
```

<210> SEQ ID NO 2
<211> LENGTH: 355
<212> TYPE: PRT
<213> ORGANISM: Homo sapiens

<400> SEQUENCE: 2

```
Met Ala Lys Leu Ile Ala Leu Thr Leu Leu Gly Met Gly Leu Ala Leu
1               5                   10                  15

Phe Arg Asn His Gln Ser Ser Tyr Gln Thr Arg Leu Asn Ala Leu Arg
            20                  25                  30

Glu Val Gln Pro Val Glu Leu Pro Asn Cys Asn Leu Val Lys Gly Ile
        35                  40                  45

Glu Thr Gly Ser Glu Asp Met Glu Ile Leu Pro Asn Gly Leu Ala Phe
    50                  55                  60

Ile Ser Ser Gly Leu Lys Tyr Pro Gly Ile Lys Ser Phe Asn Pro Asn
65                  70                  75                  80

Ser Pro Gly Lys Ile Leu Leu Met Asp Leu Asn Glu Glu Asp Pro Thr
                85                  90                  95

Val Leu Glu Leu Gly Val Thr Gly Ser Lys Phe Asp Val Ser Ser Phe
            100                 105                 110

Asn Pro His Gly Ile Ser Thr Phe Thr Asp Glu Asp Asn Ala Met Tyr
        115                 120                 125

Leu Leu Val Val Asn His Pro Asp Ala Lys Ser Thr Val Glu Leu Phe
    130                 135                 140

Lys Phe Gln Glu Glu Glu Lys Ser Leu Leu His Leu Lys Thr Ile Arg
145                 150                 155                 160

His Lys Leu Leu Pro Asn Leu Asn Asp Ile Val Ala Val Gly Pro Glu
                165                 170                 175

His Phe Tyr Gly Thr Asn Asp His Tyr Phe Leu Asp Pro Tyr Leu Gln
            180                 185                 190

Ser Trp Glu Met Tyr Leu Gly Leu Ala Trp Ser Tyr Val Val Tyr Tyr
        195                 200                 205

Ser Pro Ser Glu Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asn Thr Leu Val Asp Asn Ile Ser
            260                 265                 270

Val Asp Pro Glu Thr Gly Asp Leu Trp Val Gly Cys His Pro Asn Gly
        275                 280                 285

Met Lys Ile Phe Phe Tyr Asp Ser Glu Asn Pro Pro Ala Ser Glu Val
    290                 295                 300

Leu Arg Ile Gln Asn Ile Leu Thr Glu Glu Pro Lys Val Thr Gln Val
305                 310                 315                 320

Tyr Ala Glu Asn Gly Thr Val Leu Gln Gly Ser Thr Val Ala Ser Val
                325                 330                 335

Tyr Lys Gly Lys Leu Leu Ile Gly Thr Val Phe His Lys Ala Leu Tyr
            340                 345                 350
```

Cys Glu Leu
        355

<210> SEQ ID NO 3
<211> LENGTH: 1068
<212> TYPE: DNA
<213> ORGANISM: Homo sapiens
<220> FEATURE:
<221> NAME/KEY: CDS
<222> LOCATION: (1)..(1068)
<223> OTHER INFORMATION: Coding sequence for Human Paraoxonase (PON1)
       gene

<400> SEQUENCE: 3

| | | |
|---|---|---|
| atg gcg aag ctg att gcg ctc acc ctc ttg ggg atg gga ctg gca ctc<br>Met Ala Lys Leu Ile Ala Leu Thr Leu Leu Gly Met Gly Leu Ala Leu<br>1               5                   10                  15 | | 48 |
| ttc agg aac cac cag tct tct tac caa aca cga ctt aat gct ctc cga<br>Phe Arg Asn His Gln Ser Ser Tyr Gln Thr Arg Leu Asn Ala Leu Arg<br>            20                  25                  30 | | 96 |
| gag gta caa ccc gta gaa ctt cct aac tgt aat tta gtt aaa gga atc<br>Glu Val Gln Pro Val Glu Leu Pro Asn Cys Asn Leu Val Lys Gly Ile<br>        35                  40                  45 | | 144 |
| gaa act ggc tct gaa gac atg gag ata ctg cct aat gga ctg gct ttc<br>Glu Thr Gly Ser Glu Asp Met Glu Ile Leu Pro Asn Gly Leu Ala Phe<br>    50                  55                  60 | | 192 |
| att agc tct gga tta aag tat cct gga ata aag agc ttc aac ccc aac<br>Ile Ser Ser Gly Leu Lys Tyr Pro Gly Ile Lys Ser Phe Asn Pro Asn<br>65                  70                  75                  80 | | 240 |
| agt cct gga aaa ata ctt ctg atg gac ctg aat gaa gaa gat cca aca<br>Ser Pro Gly Lys Ile Leu Leu Met Asp Leu Asn Glu Glu Asp Pro Thr<br>                85                  90                  95 | | 288 |
| gtg ttg gaa ttg ggg atc act gga agt aaa ttt gat gta tct tca ttt<br>Val Leu Glu Leu Gly Ile Thr Gly Ser Lys Phe Asp Val Ser Ser Phe<br>            100                 105                 110 | | 336 |
| aac cct cat ggg att agc aca ttc aca gat gaa gat aat gcc atg tac<br>Asn Pro His Gly Ile Ser Thr Phe Thr Asp Glu Asp Asn Ala Met Tyr<br>        115                 120                 125 | | 384 |
| ctc ctg gtg gtg aac cat cca gat gcc aag tcc aca gtg gag ttg ttt<br>Leu Leu Val Val Asn His Pro Asp Ala Lys Ser Thr Val Glu Leu Phe<br>    130                 135                 140 | | 432 |
| aaa ttt caa gaa gaa gaa aaa tcg ctt ttg cat cta aaa acc atc aga<br>Lys Phe Gln Glu Glu Glu Lys Ser Leu Leu His Leu Lys Thr Ile Arg<br>145                 150                 155                 160 | | 480 |
| cat aaa ctt ctg cct aat ttg aat gat att gtt gct gtg gga cct gag<br>His Lys Leu Leu Pro Asn Leu Asn Asp Ile Val Ala Val Gly Pro Glu<br>                165                 170                 175 | | 528 |
| cac ttt tat ggc aca aat gat cac tat ttt ctt gac ccc tac tta caa<br>His Phe Tyr Gly Thr Asn Asp His Tyr Phe Leu Asp Pro Tyr Leu Gln<br>            180                 185                 190 | | 576 |
| tcc tgg gag atg tat ttg ggt tta gcg tgg tcg tat gtt gtc tac tat<br>Ser Trp Glu Met Tyr Leu Gly Leu Ala Trp Ser Tyr Val Val Tyr Tyr<br>        195                 200                 205 | | 624 |
| agt cca agt gaa gtt cga gtg gtg gca gaa gga ttt gat ttt gct aat<br>Ser Pro Ser Glu Val Arg Val Val Ala Glu Gly Phe Asp Phe Ala Asn<br>    210                 215                 220 | | 672 |
| gga atc aac att tca ccc gat ggc aag tat gtc tat ata gct gag ttg<br>Gly Ile Asn Ile Ser Pro Asp Gly Lys Tyr Val Tyr Ile Ala Glu Leu<br>225                 230                 235                 240 | | 720 |
| ctg gct cat aag att cat gtg tat gaa aag cat gct aat tgg act tta<br>Leu Ala His Lys Ile His Val Tyr Glu Lys His Ala Asn Trp Thr Leu | | 768 |

```
                    245                 250                 255
act cca ttg aag tcc ctt gac ttt aat acc ctc gtg gat aac ata tct        816
Thr Pro Leu Lys Ser Leu Asp Phe Asn Thr Leu Val Asp Asn Ile Ser
        260                 265                 270 gtg gat cct gag aca gga gac ctt tgg gtt gga tgc cat ccc aat ggc        864
Val Asp Pro Glu Thr Gly Asp Leu Trp Val Gly Cys His Pro Asn Gly
            275                 280                 285 atg aaa atc ttc ttc tat gac tca gag aat cct cct gca tca gag gtg        912
Met Lys Ile Phe Phe Tyr Asp Ser Glu Asn Pro Pro Ala Ser Glu Val
    290                 295                 300 ctt cga atc cag aac att cta aca gaa gaa cct aaa gtg aca cag gtt        960
Leu Arg Ile Gln Asn Ile Leu Thr Glu Glu Pro Lys Val Thr Gln Val
305                 310                 315                 320 tat gca gaa aat ggc aca gtg ttg caa ggc agt aca gtt gcc tct gtg       1008
Tyr Ala Glu Asn Gly Thr Val Leu Gln Gly Ser Thr Val Ala Ser Val
                325                 330                 335 tac aaa ggg aaa ctg ctg att ggc aca gtg ttt cac aaa gct ctt tac       1056
Tyr Lys Gly Lys Leu Leu Ile Gly Thr Val Phe His Lys Ala Leu Tyr
            340                 345                 350 tgt gag ctc taa                                                       1068
Cys Glu Leu
        355

<210> SEQ ID NO 4
<211> LENGTH: 355
<212> TYPE: PRT
<213> ORGANISM: Homo sapiens

<400> SEQUENCE: 4

Met Ala Lys Leu Ile Ala Leu Thr Leu Leu Gly Met Gly Leu Ala Leu
1               5                   10                  15

Phe Arg Asn His Gln Ser Ser Tyr Gln Thr Arg Leu Asn Ala Leu Arg
            20                  25                  30

Glu Val Gln Pro Val Glu Leu Pro Asn Cys Asn Leu Val Lys Gly Ile
        35                  40                  45

Glu Thr Gly Ser Glu Asp Met Glu Ile Leu Pro Asn Gly Leu Ala Phe
    50                  55                  60

Ile Ser Ser Gly Leu Lys Tyr Pro Gly Ile Lys Ser Phe Asn Pro Asn
65                  70                  75                  80

Ser Pro Gly Lys Ile Leu Leu Met Asp Leu Asn Glu Glu Asp Pro Thr
                85                  90                  95

Val Leu Glu Leu Gly Ile Thr Gly Ser Lys Phe Asp Val Ser Ser Phe
            100                 105                 110

Asn Pro His Gly Ile Ser Thr Phe Thr Asp Glu Asp Asn Ala Met Tyr
        115                 120                 125

Leu Leu Val Val Asn His Pro Asp Ala Lys Ser Thr Val Glu Leu Phe
    130                 135                 140

Lys Phe Gln Glu Glu Glu Lys Ser Leu Leu His Leu Lys Thr Ile Arg
145                 150                 155                 160

His Lys Leu Leu Pro Asn Leu Asn Asp Ile Val Ala Val Gly Pro Glu
                165                 170                 175

His Phe Tyr Gly Thr Asn Asp His Tyr Phe Leu Asp Pro Tyr Leu Gln
            180                 185                 190

Ser Trp Glu Met Tyr Leu Gly Leu Ala Trp Ser Tyr Val Val Tyr Tyr
        195                 200                 205

Ser Pro Ser Glu Val Arg Val Val Ala Glu Gly Phe Asp Phe Ala Asn
    210                 215                 220
```

-continued

```
Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
            245                 250                 255

Thr Pro Leu Lys Ser Leu Asp Phe Asn Thr Leu Val Asp Asn Ile Ser
            260                 265                 270

Val Asp Pro Glu Thr Gly Asp Leu Trp Val Gly Cys His Pro Asn Gly
        275                 280                 285

Met Lys Ile Phe Phe Tyr Asp Ser Glu Asn Pro Pro Ala Ser Glu Val
    290                 295                 300

Leu Arg Ile Gln Asn Ile Leu Thr Glu Glu Pro Lys Val Thr Gln Val
305                 310                 315                 320

Tyr Ala Glu Asn Gly Thr Val Leu Gln Gly Ser Thr Val Ala Ser Val
                325                 330                 335

Tyr Lys Gly Lys Leu Leu Ile Gly Thr Val Phe His Lys Ala Leu Tyr
            340                 345                 350

Cys Glu Leu
        355

<210> SEQ ID NO 5
<211> LENGTH: 20
<212> TYPE: DNA
<213> ORGANISM: Artificial Sequence
<220> FEATURE:
<223> OTHER INFORMATION: PCR primer targeted to Homo sapiens

<400> SEQUENCE: 5
gtgcatctag cacctgcttg                                                20

<210> SEQ ID NO 6
<211> LENGTH: 21
<212> TYPE: DNA
<213> ORGANISM: Artificial Sequence
<220> FEATURE:
<223> OTHER INFORMATION: PCR primer targeted to Homo sapiens

<400> SEQUENCE: 6
cagttggaag gagcaaaatg g                                              21

<210> SEQ ID NO 7
<211> LENGTH: 20
<212> TYPE: DNA
<213> ORGANISM: Artificial Sequence
<220> FEATURE:
<223> OTHER INFORMATION: PCR primer targeted to Homo sapiens

<400> SEQUENCE: 7
ggagaacttt tgtggacctg                                                20

<210> SEQ ID NO 8
<211> LENGTH: 20
<212> TYPE: DNA
<213> ORGANISM: Artificial Sequence
<220> FEATURE:
<223> OTHER INFORMATION: PCR primer targeted to Homo sapiens

<400> SEQUENCE: 8
aagtgggcat gggtatacag                                                20

<210> SEQ ID NO 9
<211> LENGTH: 20
```

<212> TYPE: DNA
<213> ORGANISM: Artificial Sequence
<220> FEATURE:
<223> OTHER INFORMATION: PCR primer targeted to Homo sapiens

<400> SEQUENCE: 9
ctcctccatg gttataaggg                                      20

<210> SEQ ID NO 10
<211> LENGTH: 21
<212> TYPE: DNA
<213> ORGANISM: Artificial Sequence
<220> FEATURE:
<223> OTHER INFORMATION: PCR primer targeted to Homo sapiens

<400> SEQUENCE: 10
cccagagtaa gaacattatt c                                    21

<210> SEQ ID NO 11
<211> LENGTH: 20
<212> TYPE: DNA
<213> ORGANISM: Artificial Sequence
<220> FEATURE:
<223> OTHER INFORMATION: PCR primer targeted to Homo sapiens

<400> SEQUENCE: 11
gactgtcact ggttcttcct                                      20

<210> SEQ ID NO 12
<211> LENGTH: 20
<212> TYPE: DNA
<213> ORGANISM: Artificial Sequence
<220> FEATURE:
<223> OTHER INFORMATION: PCR primer targeted to Homo sapiens

<400> SEQUENCE: 12
cgctacagct aaaggaaaat                                      20

<210> SEQ ID NO 13
<211> LENGTH: 20
<212> TYPE: DNA
<213> ORGANISM: Artificial Sequence
<220> FEATURE:
<223> OTHER INFORMATION: PCR primer targeted to Homo sapiens

<400> SEQUENCE: 13
gtctaaggat tgtatcggca                                      20

<210> SEQ ID NO 14
<211> LENGTH: 20
<212> TYPE: DNA
<213> ORGANISM: Artificial Sequence
<220> FEATURE:
<223> OTHER INFORMATION: PCR primer targeted to Homo sapiens

<400> SEQUENCE: 14
cactagggta acatgttaaa                                      20

<210> SEQ ID NO 15
<211> LENGTH: 20
<212> TYPE: DNA
<213> ORGANISM: Artificial Sequence
<220> FEATURE:
<223> OTHER INFORMATION: PCR primer targeted to Homo sapiens

<400> SEQUENCE: 15

```
gttgtgttac ttctagtact                                            20

<210> SEQ ID NO 16
<211> LENGTH: 20
<212> TYPE: DNA
<213> ORGANISM: Artificial Sequence
<220> FEATURE:
<223> OTHER INFORMATION: PCR primer targeted to Homo sapiens

<400> SEQUENCE: 16
ctaatgactc ttaataaagg                                            20

<210> SEQ ID NO 17
<211> LENGTH: 22
<212> TYPE: DNA
<213> ORGANISM: Artificial Sequence
<220> FEATURE:
<223> OTHER INFORMATION: PCR primer targeted to Homo sapiens

<400> SEQUENCE: 17
ggcagaatgt taaccttgga ag                                         22

<210> SEQ ID NO 18
<211> LENGTH: 20
<212> TYPE: DNA
<213> ORGANISM: Artificial Sequence
<220> FEATURE:
<223> OTHER INFORMATION: PCR primer targeted to Homo sapiens

<400> SEQUENCE: 18
catggtgcat gcgcctgtgg                                            20

<210> SEQ ID NO 19
<211> LENGTH: 20
<212> TYPE: DNA
<213> ORGANISM: Artificial Sequence
<220> FEATURE:
<223> OTHER INFORMATION: PCR primer targeted to Homo sapiens

<400> SEQUENCE: 19
gtctagatac tctccacctc                                            20

<210> SEQ ID NO 20
<211> LENGTH: 21
<212> TYPE: DNA
<213> ORGANISM: Artificial Sequence
<220> FEATURE:
<223> OTHER INFORMATION: PCR primer targeted to Homo sapiens

<400> SEQUENCE: 20
ctgaacaaga catggcaagg c                                          21
```